(12) United States Patent
Sadasivan Vijayakumari et al.

(10) Patent No.: US 8,686,207 B2
(45) Date of Patent: Apr. 1, 2014

(54) PROCESS FOR PREPARING ETHYLENE AND PROPYLENE

(75) Inventors: Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/606,204

(22) Filed: Sep. 7, 2012

(65) Prior Publication Data

US 2013/0245290 A1 Sep. 19, 2013

(30) Foreign Application Priority Data

Sep. 7, 2011 (EP) ..................................... 11180312

(51) Int. Cl.
*C07C 2/00* (2006.01)
(52) U.S. Cl.
USPC ............ 585/324; 585/326; 585/639; 585/640
(58) Field of Classification Search
USPC .................................. 585/324, 326, 639, 640
See application file for complete search history.

(56) References Cited

U.S. PATENT DOCUMENTS

| | | | |
|---|---|---|---|
| 4,207,424 A | 6/1980 | Winnick | |
| 6,049,017 A * | 4/2000 | Vora et al. ..................... | 585/324 |
| 7,932,427 B2 * | 4/2011 | Chewter et al. ............... | 585/651 |
| 8,049,054 B2 * | 11/2011 | Chewter et al. ............... | 585/643 |
| 8,153,851 B2 * | 4/2012 | Gartside et al. ............... | 585/324 |
| 8,258,358 B2 * | 9/2012 | Gartside et al. ............... | 585/324 |
| 8,507,742 B2 * | 8/2013 | Chewter et al. ............... | 585/324 |
| 2005/0107651 A1 | 5/2005 | Sher et al. | |
| 2007/0155999 A1 | 7/2007 | Pujado et al. | |
| 2007/0203380 A1 | 8/2007 | Vora et al. | |
| 2009/0105429 A1 | 4/2009 | Chewter et al. | |
| 2009/0187056 A1 | 7/2009 | Chewter et al. | |
| 2009/0187057 A1 | 7/2009 | Chewter et al. | |
| 2009/0187058 A1 | 7/2009 | Chewter et al. | |
| 2009/0187059 A1 | 7/2009 | Chewter et al. | |
| 2010/0298619 A1 | 11/2010 | Chewter et al. | |

FOREIGN PATENT DOCUMENTS

| | | |
|---|---|---|
| EP | 2108637 | 10/2009 |
| WO | 2006020083 | 2/2006 |
| WO | 2010066339 | 6/2010 |

* cited by examiner

*Primary Examiner* — Golam M Shameem

(57) ABSTRACT

The present invention provides a process for preparing ethylene and propylene, comprising the step of:
a) contacting a feed comprising methanol, ethanol and C4+ olefins with a catalyst, comprising ZSM-5 having a silica to alumina ratio in the range of from 40 to 100, at a temperature in the range of from 350 to 1000° C. to obtain a olefinic product comprising ethylene and propylene.

10 Claims, No Drawings

PROCESS FOR PREPARING ETHYLENE AND PROPYLENE

This application claims the benefit of European Application No. 11180312.8 filed Sep. 7, 2011, which is incorporated herein by reference.

FIELD OF THE INVENTION

The invention relates to a process for preparing ethylene and propylene.

BACKGROUND TO THE INVENTION

Methanol-to-olefin processes are well described in the art. Typically, methanol-to-olefin processes are used to produce predominantly ethylene and propylene. An example of such a methanol-to-olefin process is described in WO-A 2006/020083. In the process of WO-A 2006/020083, the methanol is first converted into dimethylether (DME) prior to be subjected to a conversion to olefins, thereby reducing the amount of water produced during the conversion to olefins. Both methanol and DME are suitable feedstocks for a Methanol-to-olefin process and therefore such processes are also generally referred to as oxygenate-to-olefin (OTO) processes.

Ethanol can also be converted in to ethylene. U.S. Pat. No. 4,207,424 describes a process wherein ethanol is converted to ethylene in a dehydration reaction using an alumina catalyst. U.S. Pat. No. 4,727,214 describes a process wherein ethanol is converted to ethylene using a crystalline zeolitic catalyst. Other ethanol dehydration processes have been described extensively in the prior art. A disadvantage of these processes is that only ethylene is formed in an ethanol dehydration process, where methanol-to-olefin processes convert methanol or DME to a product slate containing both ethylene and propylene. Ethanol is mentioned, among numerous other oxygenates, in several prior art documents, including for instance US20090105429, US20090187058, US20100298619, US20090187059, US20090187057, US20090187056 as an optional feedstock to an oxygenate to olefins process. However none of these documents describe the conversion of ethanol in any detail, nor do they provide any information on the expected product slate.

In EP2108637, a two step process is proposed to convert ethanol into ethylene and propylene. In the process of EP2108637, ethanol is dehydrated in a first process step. The ethanol is dehydrated to ethylene by contacting the ethanol with a silicalite (SAR 270) catalyst. In a subsequent process step the obtained ethylene is provided together with a C4+ fraction, for instance obtained from an FCC, to an olefin cracking process (OCP), wherein part of the ethylene is converted with the C4+ olefins to propylene.

In the example described in EP2108637, approximately 25 wt % of the ethylene obtained from dehydrating ethanol is converted to propylene and the effluent of the OCP reactor containing ethylene and propylene at a weight ratio of approximately 2 to 1. In contrast most methanol-to-olefin processes convert the methanol or DME to an olefinic product that contains significantly more propylene.

There is a need in the art to produce olefinic products from ethanol-comprising feedstocks with an increased propylene yield, while maintaining a high ethylene yield.

SUMMARY OF THE INVENTION

It has now been found that it is possible to convert ethanol-comprising feedstocks to an olefinic product comprising ethylene and propylene, wherein the propylene content is equal to or larger than the ethylene content in the olefinic product, wherein at least part of the propylene is produced by converting additional C4+ olefins.

Accordingly, the present invention provides a process for preparing ethylene and propylene, comprising the step of:
a) contacting a feed comprising methanol, ethanol and C4+ olefins with a catalyst, comprising ZSM-5 having a silica to alumina ratio in the range of from 40 to 100, at a temperature in the range of from 350 to 1000° C. to obtain a olefinic product comprising ethylene and propylene.

The process according to the present invention has the advantage that propylene may be produced from ethanol comprising feedstocks in a single step process. There is no need to first dehydrate the ethanol and subsequently react the obtained ethylene with an olefin in a second olefin cracking process.

In addition, it was found that providing ethanol together with methanol and butenes results in a higher ethylene and propylene yield compared to a parallel, but separate, conversion of a feed mixture of methanol and 1-butene and a feed mixture of Ethanol and 1-butene.

Furthermore, the process according to the present invention may produce an olefinic product comprising ethylene and propylene, wherein the olefinic product comprises that same amount or more propylene compared to the ethylene in the olefinic product.

DETAILED DESCRIPTION OF THE INVENTION

Ethanol may suitably be used as part of the feed to an OTO process to produce ethylene and/or propylene, i.e. an olefinic product comprising ethylene and propylene. In the process according to the present invention the ethanol is converted to the olefinic product together with methanol and C4+ olefins.

The ethanol is converted together with the other feed components to the olefinic product by contacting the feed with a catalyst comprising at least ZSM-5 at a temperature in the range of from 350 to 1000° C.

In the process according to the invention the olefinic product comprises ethylene and propylene, preferably in a weight ratio of ethylene to propylene equal to or below 1, preferably a ratio of ethylene to propylene in the range of from 1:2 to 1:1. This has the advantage that the product slate of the olefinic product is more balanced and less additional ethylene is produced in case of an increase in the propylene demand. Preferably, the olefinic product comprises advantageously at least 50 mol %, in particular at least 50 wt %, ethylene and propylene, based on total hydrocarbon content in the olefinic product.

The catalyst used in the process according to the invention comprises at least a ZSM-5 zeolite having a silica to alumina ratio of in the range of from 40 to 100, preferably of from 50 to 90. The lower silica to alumina ratio provides the catalyst with an increased activity toward the reaction of ethanol with C4+ olefin instead of the straight forward dehydration of ethanol to ethylene. The reaction of the ethanol with for instance a C4 olefin may include an alkylation resulting in a C6 olefin with is subsequently cracked to two propylene molecules.

The catalyst may comprise phosphorus, as such or in a compound, i.e. phosphorus other than any phosphorus included in the framework of the molecular sieve. The phosphorus may be introduced by pre-treating the ZSM-5 zeolite prior to formulating the catalyst and/or by post-treating the formulated catalyst comprising the ZSM-5 zeolite. Preferably, the catalyst comprising ZSM-5 comprises phosphorus as such or in a compound in an elemental amount of from 0.05-10 wt % based on the weight of the formulated catalyst. A particularly preferred catalyst comprises phosphorus-treated ZSM-5 having SAR of in the range of from 50 to 90, more preferably of from 60 to 90, even more preferably 80 to 90.

The catalyst typically also includes binder materials, matrix material and optionally fillers. Suitable matrix materials include clays, such as kaolin. Suitable binder materials include silica, alumina, silica-alumina, titania and zirconia, wherein silica is preferred due to its low acidity.

Preferably, the catalyst also comprises at least one zeolite selected from MEL, TON and MTT type zeolites, more preferably at least one of ZSM-11, ZSM-22 and ZSM-23 zeolites. It is particularly preferred that the catalyst further comprises ZSM-22 and ZSM-23. Contrary to ZSM-5, which is a multi dimensional zeolite, these are zeolites having one-dimensional 10-membered ring channels, which are known for their particular suitability to convert oxygenates, in particular methanol, to olefins in the presence of C4+ olefins.

It is preferred that the zeolites in the hydrogen form are used, e.g. HZSM-5, HZSM-22, and HZSM-23. Preferably at least 50 wt %, more preferably at least 90 wt %, still more preferably at least 95 wt % and most preferably 100 w % of the total amount of zeolite used is in the hydrogen form. It is well known in the art how to produce such zeolites in the hydrogen form.

The olefinic product comprises ethylene and propylene, but may also comprise other components, in particular C4+ olefins. Preferably, C4+ olefins are separated from the olefinic product as part of a C4+ hydrocarbon fraction and provided at least in part to step (a) of the process to form at least part of the feed to the process. Preferably, the C4+ hydrocarbon fraction comprises in the range of from 50 to 100 wt % of C4 and C5 olefins, based on the olefins in the C4+ hydrocarbon fraction, more preferably of from 50 to 100 wt % of C4 olefins, based on the olefins in the C4+ hydrocarbon fraction.

It is preferred that part of the C4+ hydrocarbon fraction is withdrawn from the process as a purge stream to purge paraffins. Paraffins present in the C4+ hydrocarbon fraction are not converted when contacted with the catalyst in step (a). As a consequence, paraffins are preferably purged to prevent a built up of paraffins in the process.

At least part of the C4+ olefins in the C4+ hydrocarbon fraction may also be provided to a further step (b) and converted to a further olefinic product comprising ethylene and propylene in a process generally referred to as an olefin cracking process (OCP) using a zeolite-comprising catalyst. Preferably, the C4+ olefins in the C4+ hydrocarbon fraction are contacted with the zeolite-comprising catalyst at a temperature in the range of from 350 to 1000° C., preferably 350 to 750° C.; and a pressure from 0.1 kPa (1 mbar) to 5 MPa (50 bar), preferably from 100 kPa (1 bar) to 1.5 MPa (15 bar). Optionally, the stream comprising C4+ olefins provided to the OCP also contains or is provided together with a diluent. Examples of suitable diluents include, but are not limited to, such as water or steam, nitrogen, argon and methane.

Any zeolite-comprising catalyst suitable for cracking olefins may be used. Preferably, the zeolite-comprising catalyst of step (b) is the same as the zeolite-comprising catalyst in step (a). By using the same catalyst for both step (a) and step (b) the catalyst regeneration facilities may be shared.

In the process according to the invention, a feed comprising methanol, ethanol and C4+ olefins may be provided to step (a).

The methanol and ethanol are preferably bio-methanol and/or bio-ethanol. The use of bio-methanol and/or bio-ethanol may contribute in reducing the carbon dioxide footprint of the process.

The C4+ olefins may for instance include comprising C4+ normal olefins and iso-olefins, for example 1-butene, 2-butene, isobutene, 1-pentene and/or 2-pentene, 2-methyl-1-butene or 2-methyl-2-butene.

Preferably, the C4+ olefins include at least C4 and/or C5 olefins, preferably at least C4 olefins. More preferably, the C4+ olefins include in the range of from 50 to 100 wt % of C4 and/or C5 olefins based on the weight of the olefins in the feed, preferably of from 50 to 100 wt % of C4 olefins based on the weight of the olefins in the feed. The olefins may be provided as an external stream providing C4+ olefins to the process, however it may also be an internal recycle stream, intended to recycle at least part of a C4+ hydrocarbon fraction from the effluent of the step (a) or the optional OCP process of step (b). Examples of external hydrocarbon streams are the C4 and C5 fractions of the effluent of a refinery unit such as thermal cracking units, catalytic cracking units, steam cracking units, naphtha (steam) cracking units, butadiene extraction units and semi (or selective-) -hydrogenation units for removal of C4 and C5 diolefins. A particularly preferred C4 hydrocarbon stream is raffinate-1.

Preferably, at least 70 wt %, preferably 90wt % of the C4+ olefins are, during normal operation, provided by a recycle stream of a C4+ hydrocarbon fraction from step (a) and optionally step (b), based on the C4+ olefins provided to step (a).

Preferably, the feed comprises methanol and ethanol and the weight ratio of methanol to ethanol in the feed is in the range of from 1:3 to 20:1, preferably of from 1:2 to 15:1.

The preferred molar ratio of oxygenate to C4+ olefin in the feed to step (a) lies in the range of from 20:1 to 1:10, more preferably in the range of from 18:1 to 1:5, still more preferably in the range of from 15:1 to 1:3, even still more preferably in the range of from 12:1 to 1:3.

The conversion of ethanol to propylene benefits from the presence of an olefin. Without wishing to be bound to any particular theory, it is believe that for instance a butylene can be alkylated by ethanol to form a hexene, which in turn may give rise to the formation of two propylene molecules. Therefore, it is preferred that for each mol of ethanol at least one mol of C4+ olefins, preferably one mol of C4 olefins, is present in the feed. More preferably, the molar ratio of ethanol to C4+ olefin in the feed to step (a), preferably C4 olefin, is in the range of from 1:1 to 1:500, preferably of from 1:1.5 to 1:200.

The feed to step (a) of process according to the invention may comprises other oxygenates.

The feed can comprise an amount of diluents. Examples of suitable diluents include, but are not limited to, such as water or steam, nitrogen, argon, paraffins and methane. Preferably steam or water is used as the diluent.

A variety of oxygenate-to-olefin (OTO) processes is known for converting oxygenates to an olefin-containing product, as already referred to above. One such process is described in WO-A 2006/020083. Processes integrating the production of oxygenates from synthesis gas and their conversion to light olefins are described in US20070203380A1 and US20070155999A1.

The reaction conditions of step (a) include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Typically the catalyst deactivates in the course of the process, primarily due to deposition of coke on the catalyst. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the zeolite. This may also apply to the catalyst used in optional step (b) of the process. Conventional catalyst regeneration techniques can be employed to remove the coke.

The catalyst particles used in the process of the present invention can have any shape known to the skilled person to be suitable for this purpose, for example it can be present in the form of spray dried catalyst particles, spheres, tablets, rings, extrudates, etc. Extruded catalysts can be applied in various shapes, such as, cylinders and trilobes. If desired, spent catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 μm, preferably 50-100 μm.

Both the OTO process of step (a) as well as the optional OCP process of step (b) may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

In step (a) of the process an olefinic product comprising ethylene and propylene is retrieved. As described herein above, in case of step (b) a further olefinic product comprising ethylene and propylene may be obtained. The ethylene and propylene may be separated from the remainder of the components in the olefinic products. Preferably, the olefinic product and further olefinic product are at least partially, and preferably fully, combined prior to separating the ethylene and propylene from the remaining components. The ethylene may be further converted into at least one of polyethylene, mono-ethylene-glycol, ethylbenzene and styrene monomer.

The propylene may be further converted into at least one of polypropylene and propylene oxide.

EXAMPLES

The invention is illustrated by the following non-limiting examples.

Example 1

Three feed mixtures comprising methanol, ethanol and 1-butane were provided as shown in Table 1:

TABLE 1

| Feed no. | molar ratio MeOH:EtOH:C4 |
|---|---|
| I* | 6:0:3 |
| II* | 0:6:3 |
| III | 3:3:3 |

*Not according to the invention

Two zeolite-comprising catalyst were tested to convert feed mixtures I to III to ethylene and propylene.

Catalyst A:
20% wt ZSM-23 having a silica to alumina molar ratio of 46
20% wt ZSM-5 having a silica to alumina molar ratio of 80.
24% wt Silica binder
36% wt Kaolin clay Catalyst B:
40% wt ZSM-5 having a silica to alumina molar ratio of 80.
24% wt Silica binder
36% wt Kaolin clay Both catalyst were treated to introduce phosphorus.

Powders of the respective catalysts were pressed into tablets and the tablets were broken into pieces and sieved. For the catalytic testing, the sieve fraction of 60-80 mesh was used.

Prior to reaction, the catalyst was treated ex-situ in air at 600° C. for 2 hours.

The reaction was performed using a quartz reactor tube of 1.8 mm internal diameter. The catalyst samples were heated in nitrogen to 525° C. and a mixture consisting of 9 vol % of reactants, i.e. methanol, ethanol and/or 1-butene, balanced in $N_2$ was passed over the catalyst at atmospheric pressure (1 bar).

The Gas Hourly Space Velocity (GHSV) is determined by the total gas flow over the catalyst weight per unit time (ml. $g_{catalyst}^{-1}.h^{-1}$). The gas hourly space velocity used in the experiments was 24,000 (ml.$g_{catalyst}^{-1}.h^{-1}$.

The effluent from the reactor was analyzed by gas chromatography (GC) to determine the product composition.

The composition has been calculated on a weight basis of all hydrocarbons analyzed.

The results are shown in Table 2.

TABLE 2

| Feed no. | Catalyst | C2= [wt %] | C3= [wt %] | C4 [wt %] | C5 [wt %] | C6+ [wt %] | Light ends [wt %] | Ratio C2=:C3= [—] |
|---|---|---|---|---|---|---|---|---|
| I* | A | 14.7 | 50.4 | 27.4 | 3.5 | 2.1 | 1.9 | 0.29 |
| II* | A | 50.2 | 20.5 | 24.5 | 3.4 | 0.8 | 0.6 | 2.45 |
| III | A | 34.6 | 35.3 | 23.5 | 4.0 | 1.5 | 1.1 | 0.98 |
| I* | B | 17.3 | 50.3 | 24.3 | 3.2 | 2.1 | 2.8 | 0.34 |
| II* | B | 48.4 | 27.8 | 18.1 | 3.4 | 1.1 | 1.2 | 1.74 |
| III | B | 34.6 | 38.4 | 19.9 | 3.5 | 1.6 | 2.0 | 0.90 |

*not according to the invention

For all tested catalyst, the oxygenate conversion was complete. No ethanol or methanol was detected in the effluent of the reactor.

As can be seen from Table 2, feeding only methanol and 1-butene results in an olefinic product with a clear excess of propylene compared to ethylene. On the contrary feeding ethanol and 1-butene leads to an olefinic product which is propylene deficient. However, by co-feeding methanol, ethanol and 1-butene, an olefinic product is obtained with an ethylene to propylene ratio below 1, while the ethylene yield remains significantly above the yields reported in the prior art, in particular EP2108637, where the final OCP effluent only comprised 30 wt % of ethylene for an propylene yield of 19 wt %.

TABLE 3

| Feed no. | Catalyst | Total yield C2= and C3= [wt %] | Yield C4 [wt %] |
|---|---|---|---|
| I and II in parallel run* | A | 67.9 | 26.0 |
| III | A | 69.9 | 23.5 |
| I and II in parallel run* | B | 71.9 | 21.2 |
| III | B | 73.0 | 19.9 |

In table 3, the combined yield of ethylene and propylene, and the yield of C4 is given based on the combined olefinic product that would be obtained from a parallel run of feed I and feed II and the olefinic product obtained from feed III.

It will be clear that by providing ethanol together with methanol and butenes results in a higher ethylene and propylene yield compared to a parallel, but separate, conversion of a feed mixture of methanol and 1-butene and a feed mixture of ethanol and 1-butene. The improved yield is obtained at the expense of the formation of C4's, as can be seen from the lower C4 yield for feed mixture III.

What is claimed is:

1. A process for preparing ethylene and propylene, comprising the step of:
   a) contacting a feed comprising methanol, ethanol and C4+ olefins with a catalyst, comprising ZSM-5 having a silica to alumina ratio in the range of from 40 to 100, at a temperature in the range of from 350 to 1000° C. to obtain a olefinic product comprising ethylene and propylene.

2. A process according to claim 1, wherein the olefinic product comprises ethylene and propylene in a weight ratio of ethylene to propylene equal to or below 1, preferably a weight ratio of ethylene to propylene in the range of from 1:2 to 1:1.

3. A process according to claim 1, wherein the molar ratio of ethanol to C4+ olefin in the feed to step is in the range of from 1:1 to 1:500.

4. A process according to claim 1, wherein the catalyst further comprises at least one zeolite selected from MEL, TON and MTT type zeolites.

5. A process according to claim 1, wherein the ZSM-5 has a silica to alumina ratio of in the range of from 60 to 90.

6. A process according to claim 1, wherein the olefinic product further comprises C4+ olefins and at least part of the C4+ olefins are provided to step (a) as part of the feed.

7. A process according to claim 1, wherein the olefinic product further comprises C4+ olefins and at least part of the C4+ olefins are provided to a further step (b) and converted to a further olefinic product comprising ethylene and propylene in an olefin cracking process using a zeolite-comprising catalyst.

8. A process according to claim 7, wherein the catalyst of step (b) is the same as the catalyst in step (a).

9. A process according to claim 1, wherein the feed comprises methanol and ethanol and the weight ratio of methanol to ethanol in the feed is in the range of from 1:3 to 20:1.

10. A process according to claim 1, wherein the ethylene is further converted into at least one of polyethylene, mono-ethylene-glycol, ethylbenzene and styrene monomer.

* * * * *